United States Patent [19]

Thomas et al.

[11] 4,321,084
[45] Mar. 23, 1982

[54] CERTAIN HALOGENATED PHENOLS AS ANTIDOTES FOR THIOCARBAMATE HERBICIDES

[75] Inventors: Victor M. Thomas; Martin D. Mahoney, both of San Jose, Calif.

[73] Assignee: Stauffer Chemical Company, Westport, Conn.

[21] Appl. No.: 836,129

[22] Filed: Sep. 23, 1977

[51] Int. Cl.³ ............................................. A01N 25/32
[52] U.S. Cl. ........................................ 71/100; 71/88; 71/94; 71/105; 71/107; 71/121; 71/122
[58] Field of Search ................ 71/100, 105, 122, 94, 71/107, 121

[56] References Cited

U.S. PATENT DOCUMENTS

| | | | |
|---|---|---|---|
| 2,913,327 | 11/1959 | Tilles et al. | 71/2.7 |
| 3,185,720 | 5/1965 | Tilles et al. | 260/455 |
| 3,198,786 | 8/1965 | Tilles et al. | 260/239 |

Primary Examiner—Catherine L. Mills
Attorney, Agent, or Firm—Harry A. Pacini

[57] ABSTRACT

Halogenated phenols of the formula

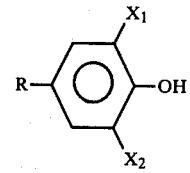

wherein each of $X_1$ and $X_2$ is halogen and R is selected from the group consisting of lower alkyl, carbalkoxy, carboxy, formyl, hydroxymethyl, trifluoromethyl, cyano and hydroxyiminomethyl, are useful as antidotes to protect crops from injury due to thiocarbamate herbicides.

31 Claims, No Drawings

CERTAIN HALOGENATED PHENOLS AS ANTIDOTES FOR THIOCARBAMATE HERBICIDES

DESCRIPTION OF THE INVENTION

This invention relates to protection of crops from injury due to thiocarbamate herbicides by use of certain halogenated phenols.

Thiocarbamate herbicides are well known, some being commercially available, and widely used in agriculture to selectively control the growth of weeds. Illustrative examples of thiocarbamate herbicides are: S-ethyl N,N-di-n-propyl thiocarbamate, S-ethyl N,N-diisobutyl thiocarbamate, S-n-propyl N,N-di-n-propyl thiocarbamate, S-ethyl-N-cyclohexyl-N-ethyl thiocarbamate, S-n-propyl N-n-butyl-N-ethyl thiocarbamate, S-ethyl hexahydro-1H-azepine carbothioate, 2,3,3-trichloroallyl N,N-diisopropyl thiocarbamate, S-isopropyl-1-(5-ethyl-2-methyl-piperidine) carbothioate, S-p-chlorobenzyl N,N-diethyl thiocarbamate, S-p-chlorobenzyl hexahydro-1H-azepine carbothioate, S-benzyl N,N-di-sec-butyl, S-p-chlorophenyl N,N-dimethyl thiocarbamate, and S-phenyl N,N-diallyl thiocarbamate. At times, however, the amount of herbicide required to adequately control weeds results in injury to the crops planted in the field where the herbicide has been applied. A recent development in this area is the discovery that certain compounds, referred to as antidotes, selectively protect crop plants from herbicidal injury while not reducing the desired control of weeds.

It has now been discovered that phenols of the formula

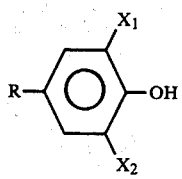

wherein each of $X_1$ and $X_2$ is halogen and R is selected from the group consisting of lower alkyl, carbalkoxy, carboxy, formyl, hydroxymethyl, trifluoromethyl, cyano and hydroximinomethyl, are useful as antidotes to protect crops from injury due to thiocarbamate herbicides. The term halogen includes chlorine, bromine, fluorine and iodine. Particularly preferred as chloride and bromine. The term carbalkoxy refers to the radical

wherein $R_1$ is lower alkyl. Lower alkyl includes straight and branched chain alkyl radicals containing 1–4 carbon atoms, i.e., methyl, ethyl, propyl, isopropyl, butyl, isobutyl, sec-butyl and tert-butyl.

The phenols used in accordance with this invention are known compounds, some being commercially available. Numerous methods of synthesis of these compounds are reported in the literature. In addition, several of the bromophenols are reported to have been isolated from marine algae.

Illustrative examples of halogenated phenols used in this invention are shown in the following Table I. The compounds are assigned compound numbers which are then used throughout the remainder of the specification.

TABLE I

| Compound No. | $X_1$ | $X_2$ | R |
|---|---|---|---|
| 1 | Br | Br | —CN |
| 2 | I | I | —CN |
| 3 | Cl | Cl | —CN |
| 4 | Br | Br | —CF$_3$ |
| 5 | Br | Br | —CH$_2$OH |
| 6 | Cl | Cl | —C(O)H |
| 7 | Cl | Cl | —CH=NOH |
| 8 | Cl | Cl | —COOH |
| 9 | Br | Br | —C(O)OC$_2$H$_5$ |
| 10 | Cl | Cl | —CH$_3$ |
| 11 | Br | Br | —CH$_3$ |
| 12 | Br | Br | —C$_2$H$_5$ |

The following test procedures were utilized to illustrate the effectiveness of these phenols in protecting crops, particularly soybeans, from injury due to thiocarbamate herbicides. The herbicides used are:

S-n-propyl N,N-di-n-propyl thiocarbamate (VERNAM®)
S-ethyl N,N-diisobutyl thiocarbamate (SUTAN®)
S-ethyl N-cyclohexyl-N-ethyl thiocarbamate (RO-NEET®) and
S-isopropyl 1-(5-ethyl-2-methyl-piperidine)carbothioate (R-12001)

The methods of antidote application employed are described more fully below and designated by the following abbreviations:

IF = In-furrow method
PPI = Pre-plant incorporated
PPIm = Pre-plant incorporated from tank-mix
PPIs = Pre-plant incorporated separate application The following abbreviations are used for crops protected by the phenols:

Ba = Barley [*Hordeum vulgare* (L.)]
Cn = Corn [*Zea maize*]
Ct = Cotton [*Gossypium hirsutum*]
Mo = Milo [*Sorghum vulgare*]
Rc = Rice [*Oryza sativa*]
Sb = Soybeans [*Glycine max*]
Wh = Wheat [*Triticum aestivum*]

As a preparatory step, the following stock solutions were prepared.

HERBICIDES

S-n-propyl N,N-di-n-propyl thiocarbamate (VERNAM® 6E)

366 milligrams of VERNAM 6E was diluted in 75 milliliters of water to provide a solution such that 1 milliliter of solution is equivalent to a rate of 1 pound per acre (lb/A) when applied to a 6"×9" flat pre-plant incorporated (PPI); similarly, 1.25 milliliter of solution is equivalent to 1.25 lb/A; 1.5 ml of solution is equivalent to 1.5 lb/A; 5 ml of solution is equivalent to 5 lb/A; 6 ml of solution is equivalent to 6 lb/A and 7 ml of solution is equivalent to 7 lb/A.

S-ethyl N-cyclohexyl-N-ethyl thiocarbamate (RO-NEET® 6E)

432 milligrams of RO-NEET 6E was diluted in 200 milliliters of water to provide a solution such that 5 milliliters of solution is equivalent to a rate of application of 3 lb/A when applied PPI to a 6"×9" flat.

S-ethyl N,N-diisobutyl thiocarbamate (SUTAN® 6E)

360 milligrams of SUTAN 6E was diluted in 100 milliliters of water to provide a solution such that 5 milliliters of solution is equivalent to a rate of application of 5 lb/A when applied PPI to a 6"×9" flat.

S-isopropyl 1-(5-ethyl-2-methylpiperidine) carbothioate (R-12001)

324 milligrams of R-12001 was diluted in 100 milliliters acetone to provide a solution such that 5 milliliters of solution is equivalent to a rate of application of 6 lb/A when applied PPI to a 6"×9" flat.

ANTIDOTES

In-Furrow Solutions 95 milligrams of each compound to be tested as an antidote was dissolved in 15 milliliters acetone so that 1.5 milliliters of solution is equivalent to a rate of 5 lb/A, 0.75 milliliters is equivalent to 2.5 lb/A, and 0.3 milliliters is equivalent to 1 lb/A when applied to a flat by the in-furrow procedure.

Pre-plant Incorporated Solutions 35 milligrams of each compound to be tested as an antidote was dissolved in 10 milliliters acetone so than 5.0 milliliters of solution is equivalent to a rate of application of 5 lb/A, 2.5 milliliters is equivalent to 2.5 lb/A and 1.0 milliliters is equivalent is 1 lb/A when applied to a flat PPI.

In-Furrow Evaluation Procedure (IF)

Small flats (6"×9") were filled with Felton loamy sand soil. The soil from each flat was transferred to a five-gallon cement mixer and herbicide stock solution was added in an amount to provide the rate of application indicated in Table II. After the herbicide incorporation, the soil was placed back into the flats with the exception of about one pint of soil which was reserved for later use to cover the seeds after planting.

Rows ¼-inch deep were made length-wise in each treated flat and seeds of several crops were placed in the rows. After seeding, the flats were sectioned into two equal portions. Antidote stock solution of the test compound, in an amount to provide the rate of application indicated in Table II, was atomized directly onto the exposed seed and soil in the open furrow in one-half of the flat. The seeds were covered with the one pint of soil which had been removed earlier. The flats were placed in a greenhouse, maintained at 70°-90° F., and watered by sprinkling as needed. After four weeks the percent injury of each of the crops in the antidote treated half of the flat was determined. Antidotal activity was observed by comparing the growth of the crops in the treated section with that of the untreated half of the flat. In each test a control flat containing herbicide treated soil was prepared and planted with the crop seed. At the end of four weeks the percent injury of the crops in the control flat was determined. The injury rating of the crops in the antidote treated half of the treated flat and the injury rating of the crops in the control flat is reported in Table II.

Pre-plant Incorporation Evaluation Procedure (PPI)

(A). Separate Application (PPIs)

Flats (6"×9") were filled with Felton loamy sand soil. The soil from each was placed in a five-gallon cement mixer. While the soil was mixing, stock solution of herbicide to provide the rate of application indicated in Table II, was added to prepare the soil for the untreated, or control, flats. To prepare the soil for antidote treated flats, separate stock solutions of herbicide and antidote were added to the mixing soil. After mixing the soil was transferred to the flats and crop seeds planted. The flats were placed in the greenhouse and maintained at a temperature of 70°-90° F. Flats were watered by sprinkling as needed. After four weeks the percent injury of the crops in the antidote treated flats and the percent injury of the crops in the untreated, or control flats, were recorded. The results, in Table II, show the identity of the crops protected and the injury ratings.

(B) Tank-Mix Application (PPIm)

The procedure described above was repeated with the exception that to prepare the antidote treated flats herbicide and antidote stock solutions were mixed together prior to being added to the soil in the cement mixer. The percent injury of the crops in the antidote treated flats and the percent injury of the crops in the untreated, or control, flats were recorded. The results, in Table II, show the identity of the crops protected and the injury ratings.

TABLE II

| Antidote | Rate (lb/A) | Application | Herbicide | Rate (lb/A) | Application | Crop | % Injury Antidote Flat | % Injury Control Flat |
|---|---|---|---|---|---|---|---|---|
| 1 | 5 | IF | VERNAM | 5 | PPI | Sb | 10 | 40 |
| 1 | 1 | IF | VERNAM | 1 | PPI | Ba | 65 | 80 |
| 1 | 0.5 | IF | VERNAM | 5 | PPI | Sb | 0 | 10 |
| 1 | 1 | IF | VERNAM | 5 | PPI | Sb | 30 | 40 |
| 1 | 5 | PPIm | VERNAM | 7 | PPIm | Sb | 50 | 60 |
| 1 | 5 | PPIs | VERNAM | 6 | PPIs | Sb | 0 | 50 |
| 1 | 2.5 | PPIm | VERNAM | 7 | PPIm | Sb | 50 | 60 |
| 1 | 2.5 | PPIs | VERNAM | 6 | PPIs | Sb | 10 | 50 |
| 1 | 1 | PPIs | VERNAM | 6 | PPIs | Sb | 40 | 50 |
| 1 | 1 | PPIm | SUTAN | 5 | PPIm | Ct | 35 | 50 |
| 2 | 5 | PPIs | VERNAM | 5 | PPIs | Sb | 20 | 40 |
| 2 | 1 | PPIm | VERNAM | 1.5 | PPIm | Ct | 20 | 50 |
| 2 | 1 | PPIm | VERNAM | 5 | PPIm | Sb | 0 | 50 |
| 2 | 5 | PPIm | VERNAM | 7 | PPIm | Sb | 50 | 60 |
| 2 | 2.5 | PPIm | VERNAM | 7 | PPIm | Sb | 40 | 60 |
| 2 | 5 | PPIm | SUTAN | 5 | PPIm | Ct | 20 | 50 |
| 2 | 1 | PPIm | SUTAN | 5 | PPIm | Ct | 25 | 50 |

TABLE II-continued

| Antidote | Rate (lb/A) | Application | Herbicide | Rate (lb/A) | Application | Crop | % Injury Antidote Flat | % Injury Control Flat |
|---|---|---|---|---|---|---|---|---|
| 3 | 5 | PPIm | VERNAM | 6 | PPIm | Sb | 20 | 50 |
| 3 | 5 | PPIm | VERNAM | 7 | PPIm | Sb | 40 | 60 |
| 3 | 2.5 | PPIm | VERNAM | 6 | PPIm | Sb | 30 | 50 |
| 3 | 1 | PPIm | VERNAM | 6 | PPIm | Sb | 40 | 50 |
| 4 | 5 | IF | VERNAM | 1 | PPI | Mo | 30 | 85 |
| 4 | 5 | IF | VERNAM | 1 | PPI | Ba | 30 | 55 |
| 4 | 5 | IF | VERNAM | 6 | PPI | Cn | 50 | 90 |
| 4 | 5 | PPIm | VERNAM | 1.25 | PPIm | Sb | 40 | 50 |
| 4 | 5 | PPIm | RO-NEET | 3 | PPIm | Mo | 60 | 75 |
| 4 | 5 | IF | RO-NEET | 4 | PPI | Mo | 40 | 60 |
| 5 | 5 | IF | VERNAM | 1 | PPI | Mo | 50 | 96 |
| 5 | 5 | IF | VERNAM | 5 | PPI | Cn | 70 | 90 |
| 5 | 2 | IF | VERNAM | 1 | PPI | Wh | 60 | 90 |
| 5 | 2 | IF | VERNAM | 1 | PPI | Rc | 80 | 100 |
| 5 | 2 | IF | VERNAM | 5 | PPI | Cn | 40 | 60 |
| 5 | 0.5 | IF | VERNAM | 1 | PPI | Wh | 60 | 90 |
| 5 | 0.5 | IF | VERNAM | 1 | PPI | Ba | 70 | 80 |
| 5 | 5 | PPIm | VERNAM | 6 | PPIm | Sb | 10 | 50 |
| 5 | 1 | PPIm | VERNAM | 6 | PPIm | Sb | 40 | 50 |
| 6 | 5 | IF | VERNAM | 6 | PPI | Cn | 60 | 85 |
| 6 | 5 | IF | VERNAM | 6 | PPI | Sb | 35 | 60 |
| 6 | 5 | PPIm | VERNAM | 6 | PPIm | Sb | 40 | 50 |
| 7 | 5 | IF | VERNAM | 1.25 | PPI | Wh | 70 | 95 |
| 7 | 5 | IF | VERNAM | 1.25 | PPI | Ba | 30 | 70 |
| 7 | 5 | IF | VERNAM | 1.25 | PPI | Ct | 30 | 50 |
| 7 | 5 | IF | VERNAM | 6 | PPI | Sb | 10 | 50 |
| 7 | 2.5 | PPIm | VERNAM | 6 | PPIm | Sb | 40 | 50 |
| 7 | 2.5 | PPIm | R-12001 | 6 | PPIm | Ct | 50 | 70 |
| 8 | 5 | IF | VERNAM | 5 | PPI | Sb | 50 | 60 |
| 8 | 5 | PPIm | VERNAM | 1.5 | PPIm | Ct | 40 | 50 |
| 8 | 1 | PPIm | VERNAM | 1.5 | PPIm | Ct | 30 | 50 |
| 9 | 5 | IF | VERNAM | 6 | PPI | Sb | 30 | 55 |
| 9 | 5 | PPIm | VERNAM | 7 | PPIm | Sb | 40 | 60 |
| 10 | 5 | IF | VERNAM | 1 | PPI | Wh | 60 | 80 |
| 10 | 5 | IF | VERNAM | 1.5 | PPI | Ct | 0 | 50 |
| 11 | 1 | IF | VERNAM | 1.5 | PPI | Ct | 30 | 50 |
| 12 | 5 | IF | VERNAM | 1.25 | PPI | Ba | 60 | 90 |

The phenols were also tested to determine their effect on the activity of thiocarbamates in controlling undesired vegetation, specifically, the weeds watergrass (*Enchinochloa crusgalli*) (WG), foxtail (*Setaria viridis*) (FT), Johnson grass (*Sorghum halepense*) (JG), nutsedge (*Cyperus sp.*) (NS), and shattercane (*Sorghum bicolor*) (SC). The evaluation procedures described above were followed with the exception that weed seeds were planted in the treated and untreated, or control, flats. After four weeks the injury ratings were noted. The results are shown in Table III. No protection of the weeds by the antidote compound is indicated by "√" and where some protection of the weeds by the antidote was observed the % injury in the antidoted flats and the % injury in the untreated flats are reported.

TABLE III

| Antidote | Rate lb/A | Application | Herbicide | Rate lb/A | Application | WG | FT | JG | NS | SC |
|---|---|---|---|---|---|---|---|---|---|---|
| 1 | 5.0 | PPIs | VERNAM | 1.25 | PPIs | √ | √ | | | |
|  | 2.5 | PPIs | VERNAM | 1.25 | PPIs | √ | √ | | | |
|  | 1.0 | PPIs | VERNAM | 1.25 | PPIs | √ | √ | | | |
| 4 | 5.0 | PPIs | VERNAM | 1.25 | PPIs | √ | √ | | | |
|  | 2.5 | PPIs | VERNAM | 1.25 | PPIs | √ | √ | | | |
|  | 1.0 | PPIs | VERNAM | 1.25 | PPIs | √ | √ | | | |
| 7 | 5.0 | PPIs | VERNAM | 1.25 | PPIs | √ | √ | | | |
|  | 2.5 | PPIs | VERNAM | 1.25 | PPIs | √ | √ | | | |
|  | 1.0 | PPIs | VERNAM | 1.25 | PPIs | √ | √ | | | |
| 1 | 5.0 | PPIs | SUTAN | 5.0 | PPIs | √ | √ | √ | √ | |
|  | 1.0 | PPIs | SUTAN | 5.0 | PPIs | √ | √ | √ | √ | |
| 2 | 5.0 | PPIs | SUTAN | 5.0 | PPIs | √ | √ | √ | √ | |
|  | 1.0 | PPIs | SUTAN | 5.0 | PPIs | √ | √ | √ | √ | |
| 5 | 5.0 | PPIs | SUTAN | 5.0 | PPIs | √ | √ | | | |
|  | 1.0 | PPIs | SUTAN | 5.0 | PPIs | √ | √ | | | |
| 10 | 5.0 | PPIs | SUTAN | 5.0 | PPIs | √ | √ | | | |
|  | 1.0 | PPIs | SUTAN | 5.0 | PPIs | √ | √ | | | |
| 1 | 1.0 | PPIs | RO-NEET | 3.0 | PPIs | √ | | | | √ |
|  | 2.5 | PPIs | RO-NEET | 3.0 | PPIs | √ | | | | √ |
|  | 5.0 | PPIs | RO-NEET | 3.0 | PPIs | √ | | | | √ |
| 2 | 1.0 | PPIs | RO-NEET | 3.0 | PPIs | √ | | | | √ |
|  | 2.5 | PPIs | RO-NEET | 3.0 | PPIs | √ | | | | √ |
|  | 5.0 | PPIs | RO-NEET | 3.0 | PPIs | √ | | | | √ |
| 4 | 1.0 | PPIs | RO-NEET | 3.0 | PPIs | √ | | | | √ |
|  | 2.5 | PPIs | RO-NEET | 3.0 | PPIs | √ | | | | √ |
|  | 5.0 | PPIs | RO-NEET | 3.0 | PPIs | √ | | | | √ |

TABLE III-continued

| Antidote | Rate lb/A | Application | Herbicide | Rate lb/A | Application | WG | FT | JG | NS | SC |
|---|---|---|---|---|---|---|---|---|---|---|
| 5 | 1.0 | PPIs | RO-NEET | 3.0 | PPIs | ✓ | ✓ | | | |
| | 2.5 | PPIs | RO-NEET | 3.0 | PPIs | ✓ | ✓ | | | |
| | 5.0 | PPIs | RO-NEET | 3.0 | PPIs | ✓ | ✓ | | | |
| 6 | 1.0 | PPIs | RO-NEET | 3.0 | PPIs | ✓ | ✓ | | | |
| | 2.5 | PPIs | RO-NEET | 3.0 | PPIs | ✓ | ✓ | | | |
| | 5.0 | PPIs | RO-NEET | 3.0 | PPIs | ✓ | ✓ | | | |
| 7 | 1.0 | PPIs | RO-NEET | 3.0 | PPIs | ✓ | ✓ | | | |
| | 2.5 | PPIs | RO-NEET | 3.0 | PPIs | ✓ | ✓ | | | |
| | 5.0 | PPIs | RO-NEET | 3.0 | PPIs | ✓ | ✓ | | | |
| 9 | 1.0 | PPIs | RO-NEET | 3.0 | PPIs | ✓ | ✓ | | | |
| | 2.5 | PPIs | RO-NEET | 3.0 | PPIs | ✓ | ✓ | | | |
| | 5.0 | PPIs | RO-NEET | 3.0 | PPIs | ✓ | ✓ | | | |
| 1 | 0.5 | PPIs | VERNAM | 6 | PPIs | ✓ | ✓ | | | |
| | 1.0 | PPIs | VERNAM | 6 | PPIs | ✓ | ✓ | | | |
| | 2.5 | PPIs | VERNAM | 6 | PPIs | ✓ | ✓ | | | |
| | 5.0 | PPIs | VERNAM | 6 | PPIs | ✓ | ✓ | | | |
| 3 | 1.0 | PPIs | VERNAM | 6 | PPIs | ✓ | ✓ | | | |
| | 2.5 | PPIs | VERNAM | 6 | PPIs | ✓ | ✓ | | | |
| | 5.0 | PPIs | VERNAM | 6 | PPIs | ✓ | ✓ | | | |
| 4 | 1.0 | PPIs | VERNAM | 6 | PPIs | ✓ | ✓ | | | |
| | 2.5 | PPIs | VERNAM | 6 | PPIs | ✓ | ✓ | | | |
| | 5.0 | PPIs | VERNAM | 6 | PPIs | ✓ | ✓ | | | |
| 5 | 0.5 | PPIs | VERNAM | 6 | PPIs | ✓ | ✓ | | | |
| | 1.0 | PPIs | VERNAM | 6 | PPIs | ✓ | ✓ | | | |
| | 2.5 | PPIs | VERNAM | 6 | PPIs | ✓ | ✓ | | | |
| | 5.0 | PPIs | VERNAM | 6 | PPIs | ✓ | ✓ | | | |
| 6 | 1.0 | PPIs | VERNAM | 6 | PPIs | ✓ | ✓ | | | |
| | 2.5 | PPIs | VERNAM | 6 | PPIs | ✓ | ✓ | | | |
| | 5.0 | PPIs | VERNAM | 6 | PPIs | ✓ | ✓ | | | |
| 7 | 1.0 | PPIs | VERNAM | 6 | PPIs | ✓ | ✓ | | | |
| | 2.5 | PPIs | VERNAM | 6 | PPIs | ✓ | ✓ | | | |
| | 5.0 | PPIs | VERNAM | 6 | PPIs | ✓ | ✓ | | | |
| 9 | 1.0 | PPIs | VERNAM | 6 | PPIs | ✓ | ✓ | | | |
| | 2.5 | PPIs | VERNAM | 6 | PPIs | ✓ | ✓ | | | |
| | 5.0 | PPIs | VERNAM | 6 | PPIs | ✓ | ✓ | | | |
| 1 | 2.5 | PPIs | VERNAM | 7 | PPIs | ✓ | ✓ | | | |
| | 5.0 | PPIs | VERNAM | 7 | PPIs | ✓ | ✓ | | | |
| 2 | 2.5 | PPIs | VERNAM | 7 | PPIs | ✓ | ✓ | | | |
| | 5.0 | PPIs | VERNAM | 7 | PPIs | ✓ | ✓ | | | |
| 3 | 2.5 | PPIs | VERNAM | 7 | PPIs | ✓ | ✓ | | | |
| | 5.0 | PPIs | VERNAM | 7 | PPIs | ✓ | ✓ | | | |
| 4 | 2.5 | PPIs | VERNAM | 7 | PPIs | ✓ | ✓ | | | |
| | 5.0 | PPIs | VERNAM | 7 | PPIs | ✓ | ✓ | | | |
| 5 | 2.5 | PPIs | VERNAM | 7 | PPIs | ✓ | ✓ | | | |
| | 5.0 | PPIs | VERNAM | 7 | PPIs | ✓ | ✓ | | | |
| 9 | 2.5 | PPIs | VERNAM | 7 | PPIs | ✓ | ✓ | | | |
| | 5.0 | PPIs | VERNAM | 7 | PPIs | ✓ | ✓ | | | |
| 1 | 1.0 | PPIs | VERNAM | 2 | PPIs | | 60/70 | ✓ | | |
| | 5.0 | PPIs | VERNAM | 2 | PPIs | | 60/70 | ✓ | | |
| 2 | 1.0 | PPIs | VERNAM | 2 | PPIs | | 60/70 | ✓ | | |
| | 5.0 | PPIs | VERNAM | 2 | PPIs | | 60/70 | ✓ | | |
| 5 | 1.0 | PPIs | VERNAM | 2 | PPIs | | ✓ | ✓ | | |
| | 5.0 | PPIs | VERNAM | 2 | PPIs | | ✓ | ✓ | | |
| 10 | 1.0 | PPIs | VERNAM | 2 | PPIs | | ✓ | ✓ | | |
| | 5.0 | PPIs | VERNAM | 2 | PPIs | | ✓ | ✓ | | |
| 1 | 1.0 | PPIs | R-12001 | 6 | PPIs | | ✓ | ✓ | | |
| | 2.5 | PPIs | R-12001 | 6 | PPIs | | ✓ | ✓ | | |
| | 5.0 | PPIs | R-12001 | 6 | PPIs | | ✓ | ✓ | | |
| 2 | 1.0 | PPIs | R-12001 | 6 | PPIs | | ✓ | ✓ | | |
| | 2.5 | PPIs | R-12001 | 6 | PPIs | | ✓ | ✓ | | |
| | 5.0 | PPIs | R-12001 | 6 | PPIs | | ✓ | ✓ | | |
| 7 | 1.0 | PPIs | R-12001 | 6 | PPIs | | ✓ | ✓ | | |
| | 2.5 | PPIs | R-12001 | 6 | PPIs | | ✓ | ✓ | | |
| | 5.0 | PPIs | R-12001 | 6 | PPIs | | ✓ | ✓ | | |

In general, antidotes are used in a formulation containing the antidote and an inert carrier. The herbicide can be included in the same formulation if desired. Such formulations can take the form of dusts, wettable powders, granules, solutions of emulsifiable concentrates. Numerous methods of antidote application are well known, for example, the antidote can be incorporated into the soil before, after or simultaneously with the herbicide. Solutions of antidote and herbicide can also be combined to form a tank mix which can be applied onto the surface of the soil or incorporated into the soil. In another method, the antidote can be directly applied into the seed furrow before or after crop seed placement, prior to covering the seeds with soil. This in-furrow method economically and effectively places the antidote immediately adjacent the crop seed to be protected from herbicidal injury. The in-furrow application can take place before or after herbicide has been applied to the soil. It is also possible to treat the crop seeds with the antidote prior to planting.

As used in this specification, the term herbicide refers to a compound that selectively controls, prevents, or inhibits the growth of vegetation or plants. Herbicides are generally applied to the soil wherein control of undesired vegetation such as weeds is sought. In agricultural use, the herbicide can be applied to the soil before, after or simultaneously with planting of the crop seeds. The amount of herbicide employed in a given situation will depend on the particular herbicide used, the crop to be grown in the field, the types of weeds to be controlled and the degree of control desired. Herbicides are usually employed at a rate of about 0.05 to about 50 pounds per acre with a rate of about 1.0 to about 20 pounds per acre being preferred.

The term herbicide antidote refers to a compound which, when applied to the crop seed or the soil in which the crop seed is or will be planted, counteracts the growth controlling injurious effect of the herbicide on the crop. The term antidotally effective amount refers to the amount of the antidote which when applied to the crop seed or soil achieves the desired protection of the crop. This amount will vary widely, depending on the particular herbicide used and the method of application of the antidote. One skilled in the art, with the teaching of this specification before him, will be able, without undue experimentation, to determine the antidotally effective amount of the particular phenol to protect crops from injury by thiocarbamate herbicides. The amount of antidote employed can range from about 0.05 to about 50 pounds per acre. A rate of application of about 1 to about 10 pounds per acre is preferred.

In general the amount of antidote compound used in porportion to the amount of herbicide used will be from about 0.001 to about 30, preferably about 0.01 to about 20, parts by weight of antidote per part herbicide.

What is claimed is:

1. A herbicidal composition comprising a thiocarbamate herbicide and a non-phytotoxic antidotally effective amount of a halogenated phenol of the formula

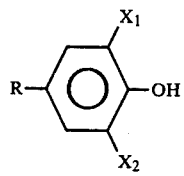

wherein each of $X_1$ and $X_2$ is halogen and R is selected from the group consisting of lower alkyl, carbalkoxy, carboxy, formyl, hydroxymethyl, trifluoromethyl, cyano and hydroxyiminomethyl; said phenol being antidotally active with said thiocarbamate herbicide compound.

2. The composition of claim 1 wherein the thiocarbamate is selected from the group consisting of S-n-propyl N,N-di-n-propyl thiocarbamate, S-ethyl N,N-diisobutyl thiocarbamate, S-ethyl N-cyclohexyl-N-ethyl thiocarbamate, and S-isopropyl 1-(5-ethyl-2-methylpiperidine) carbothioate.

3. The composition of claim 2 wherein said thiocarbamate is S-n-propyl N,N-di-n-propyl thiocarbamate.

4. The composition of claim 1 wherein $X_1$ is Br, $X_2$ is Br, and R is —CN.

5. The composition of claim 1 wherein $X_1$ is I, $X_2$ is I, and R is —CN.

6. The composition of claim 1 wherein $X_1$ is Cl, $X_2$ is Cl, and R is —CN.

7. The composition of claim 1 wherein $X_1$ is Br, $X_2$ is Br, and R is —CF$_3$.

8. The composition of claim 1 wherein $X_1$ is Br, $X_2$ is Br, and R is —CH$_2$OH.

9. The composition of claim 1 wherein $X_1$ is Cl, $X_2$ is Cl, and R is —C(O)H.

10. The composition of claim 1 wherein $X_1$ is Cl, $X_2$ is Cl, and R is —CH=NOH.

11. The composition of claim 1 wherein $X_1$ is Cl, $X_2$ is Cl, and R is —COOH.

12. The composition of claim 1 wherein $X_1$ is Br, $X_2$ is Br, and R is —C(O)OC$_2$H$_5$.

13. The composition of claim 1 wherein $X_1$ is Cl, $X_2$ is Cl, and R is —CH$_3$.

14. The composition of claim 1 wherein $X_1$ is Br, $X_2$ is Br, and R is —CH$_3$.

15. The composition of claim 1 wherein $X_1$ is Br, $X_2$ is Br, and R is —C$_2$H$_5$.

16. A method of protecting crops from injury from a thiocarbamate herbicide which comprises applying to the soil the herbicidal composition of claim 1.

17. A method of protecting crops from injury from a thiocarbamate herbicide which comprises applying to the soil a herbicidally effective amount of the thiocarbamate herbicide and a non-phytotoxic antidotally effective amount of a halogenated phenol of the formula

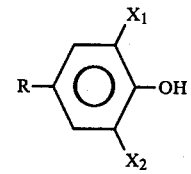

wherein each of $X_1$ and $X_2$ is halogen and R is selected from the group consisting of lower alkyl, carbalkoxy, carboxy, formyl, hydroxymethyl, trifluoromethyl, cyano and hydroxyiminomethyl.

18. The method of claim 17 wherein said thiocarbamate is selected from the group consisting of S-n-propyl N,N-di-n-propyl thiocarbamate, S-ethyl N,N-diisobutyl thiocarbamate, S-ethyl N-cyclohexyl-N-ethyl thiocarbamate, and S-isopropyl 1-(5-ethyl-2-methylpiperidine) carbothiate.

19. The method of claim 18 wherein said thiocarbamate is S-n-propyl N,N-di-n-propyl thiocarbamate.

20. The method of claim 17 wherein $X_1$ is Br, $X_2$ is Br, and R is —CN.

21. The method of claim 17 wherein $X_1$ is I, $X_2$ is I, and R is —CN.

22. The method of claim 17 wherein $X_1$ is Cl, $X_2$ is Cl, and R is —CN.

23. The method of claim 17 wherein $X_1$ is Br, $X_2$ is Br, and R is —CF$_3$.

24. The method of claim 17 wherein $X_1$ is Br, $X_2$ is Br, and R is —CH$_2$OH.

25. The method of claim 17 wherein $X_1$ is Cl, $X_2$ is Cl, and R is —C(O)H.

26. The method of claim 17 wherein $X_1$ is Cl, $X_2$ is Cl, and R is —CH-NOH.

27. The method of claim 17 wherein $X_1$ is Cl, $X_2$ is Cl, and R is —COOH.

28. The method of claim 17 wherein $X_1$ is Br, $X_2$ is Br, and R is —C(O)OC$_2$H$_5$.

29. The method of claim 17 wherein $X_1$ is Cl, $X_2$ is Cl, and R is —CH$_3$.

30. The method of claim 17 wherein $X_1$ is Br, $X_2$ is Br, and R is —CH$_3$.

31. The method of claim 17 wherein $X_1$ is Br, $X_2$ is Br, and R is —C$_2$H$_5$.

* * * * *